United States Patent
Elnajjar et al.

(10) Patent No.: US 11,702,447 B2
(45) Date of Patent: Jul. 18, 2023

(54) METHODS FOR PRODUCING COLLAGEN

(71) Applicant: AVICENNA NUTRACEUTICAL, LLC, Alpharetta, GA (US)

(72) Inventors: Ali Elnajjar, Sandy Springs, GA (US); Ali Mourad, Duluth, GA (US); Mark Ernst Brandt, Terre Haute, IN (US); Christopher Lippelt, Greenwood, IN (US)

(73) Assignee: AVICENNA NUTRACEUTICAL, INC., Alpharetta, GA (US)

( * ) Notice: Subject to any disclaimer, the term of this patent is extended or adjusted under 35 U.S.C. 154(b) by 586 days.

(21) Appl. No.: 16/611,937

(22) PCT Filed: May 10, 2018

(86) PCT No.: PCT/US2018/031941
§ 371 (c)(1),
(2) Date: Nov. 8, 2019

(87) PCT Pub. No.: WO2018/209008
PCT Pub. Date: Nov. 15, 2018

(65) Prior Publication Data
US 2021/0079038 A1    Mar. 18, 2021

Related U.S. Application Data

(60) Provisional application No. 62/504,632, filed on May 11, 2017.

(51) Int. Cl.
*C07K 1/30* (2006.01)
*C07K 14/78* (2006.01)

(52) U.S. Cl.
CPC .............. *C07K 1/30* (2013.01); *C07K 14/78* (2013.01); *C12Y 304/23001* (2013.01)

(58) Field of Classification Search
CPC .... A23J 1/002; A23J 1/10; A23J 3/342; A23L 29/284; A61K 35/57; A61K 8/042; A61K 8/65; A61Q 19/08; C07K 14/465; C07K 14/78; C07K 1/30; C12Y 304/23001
See application file for complete search history.

(56) References Cited

U.S. PATENT DOCUMENTS

| | | | |
|---|---|---|---|
| 4,331,766 A | 5/1982 | Becker et al. | |
| 4,424,208 A * | 1/1984 | Wallace | C07K 14/78 530/356 |
| 4,804,745 A | 2/1989 | Koepff et al. | |
| 5,399,347 A | 3/1995 | Trentham et al. | |
| 5,529,786 A | 6/1996 | Moore | |
| 5,571,499 A | 11/1996 | Hafler et al. | |
| 5,571,500 A | 11/1996 | Hafler et al. | |
| 5,637,321 A | 6/1997 | Moore | |
| 5,641,473 A | 6/1997 | Hafler et al. | |
| 5,641,474 A | 6/1997 | Hafler et al. | |
| 5,645,820 A | 7/1997 | Hafler et al. | |
| 5,645,851 A | 7/1997 | Moore | |
| 5,720,955 A | 2/1998 | Weiner et al. | |
| 5,733,547 A | 3/1998 | Weiner et al. | |
| 5,783,188 A | 7/1998 | Weiner et al. | |
| 5,840,848 A | 11/1998 | Sturrock et al. | |
| 5,843,445 A | 12/1998 | Weiner et al. | |
| 5,856,446 A | 1/1999 | Weiner et al. | |
| 5,869,093 A | 2/1999 | Weiner et al. | |
| 5,925,736 A | 7/1999 | Neff et al. | |
| 6,010,722 A | 1/2000 | Matsumoto et al. | |
| 6,019,971 A | 2/2000 | Weiner et al. | |
| 6,025,327 A | 2/2000 | Alkayali | |
| 6,162,787 A | 12/2000 | Sorgente et al. | |
| 6,165,983 A | 12/2000 | Klaus | |
| 6,323,319 B1 | 11/2001 | Alkayali | |
| 6,780,841 B2 | 8/2004 | Ishaq | |
| 6,838,440 B2 | 1/2005 | Stiles et al. | |
| 6,844,424 B1 | 1/2005 | Mollard et al. | |
| 6,894,029 B1 | 5/2005 | Hsieh | |
| 7,083,820 B2 | 8/2006 | Schilling et al. | |
| 7,091,180 B2 | 8/2006 | Ishaq | |
| 7,671,041 B2 | 3/2010 | Vouland et al. | |
| 7,759,310 B2 | 7/2010 | Gu et al. | |
| 7,799,348 B2 | 9/2010 | Ishaq | |
| 7,846,487 B2 | 12/2010 | Schilling et al. | |

(Continued)

FOREIGN PATENT DOCUMENTS

| | | |
|---|---|---|
| CN | 101343653 | 1/2009 |
| WO | 9725435 | 7/1997 |

OTHER PUBLICATIONS

Nagai, T. et al., "Isolation and characterization of collagen from rhizostomous jellyfish (*Rhopilema asamushi*)," 2000, Food Chemistry, 70:205-208.
Lin, Y.K. et al., "Effects of pepsin digestion at different temperatures and times on properties of telopeptide-poor collagen from bird feet," 2006, Food Chemistry, 94:621-625.
International Search Report and Written Opinion for PCT/US2018/031941 dated Jul. 20, 2018 (10pp).
Schmidt et al., Collagen Extraction Process., International Food Research Journal, vol. 23 No. 3., Jan. 1, 2016.
Cao Hui et al., Purification and characterization of type II collagen from chick sternal cartilage., Food Chemistry, Elsevier Ltd, NL, vol. 108, No. 2, Sep. 18, 2007.
Maria Helena Santos et al., Extraction and characterization of highly purified collagen from bovine pericardium for potential bioengineering applications., Materials Science and Engineering C, vol. 33, No. 2, Mar. 1, 2013.

(Continued)

*Primary Examiner* — Blaine Lankford
(74) *Attorney, Agent, or Firm* — Thomas|Horstemeyer, LLP

(57) ABSTRACT

Disclosed herein are methods for efficiently isolating collagen form a collagen source. The methods are inexpensive and do not require the use of proteolytic enzymes, decolorizing agents, antibacterial and antifungal agents, and the like. Further, the collagen produced by the methods described herein is substantially free of odor and discoloration. Still further, the collagen produced by the methods described herein is suitable to be used in cosmetics, food products, and pharmaceuticals or nutritional supplements.

38 Claims, No Drawings

(56) References Cited

U.S. PATENT DOCUMENTS

| | | |
|---|---|---|
| 7,919,456 B2 | 4/2011 | Ghosh |
| 8,344,106 B1 | 1/2013 | Summers et al. |
| 8,470,975 B2 | 6/2013 | Sumers et al. |
| 8,563,045 B2 | 10/2013 | Ishaq |
| 8,652,530 B1 | 2/2014 | Moore |
| 8,703,174 B2 | 4/2014 | Hurwitz |
| 8,735,373 B2 | 5/2014 | Pizzoni |
| 8,748,499 B2 | 6/2014 | Lau et al. |
| 2005/0009734 A1 | 1/2005 | Stiles |
| 2007/0219128 A1 | 9/2007 | Chen et al. |
| 2011/0135699 A1 | 6/2011 | Dick et al. |
| 2013/0123468 A1* | 5/2013 | Moriyama ............... A23L 2/66 530/356 |
| 2013/0252899 A1 | 9/2013 | Hausmanns et al. |
| 2014/0107064 A1 | 4/2014 | Pizzoni |
| 2014/0113861 A1 | 4/2014 | Ferrer et al. |
| 2014/0140963 A1 | 5/2014 | Moore |

OTHER PUBLICATIONS

Woo et al: Extraction optimization and properties of collagen from yellowfin tuna (*Thunnus albacares*) dorsal skin., Food Hydrocolloids, Elsevier BV, NL, vol. 22, No. 5, Feb. 25, 2008.
European Search Report dated Feb. 2, 2021 for EP Application No. 18798463.8.

* cited by examiner

METHODS FOR PRODUCING COLLAGEN

CROSS REFERENCE TO RELATED APPLICATIONS

This application claims priority upon U.S. provisional application Ser. No. 62/504,632 filed May 11, 2017. This application is hereby incorporated by reference in its entirety for all of its teachings.

BACKGROUND

Collagen preparations have been used in a variety of capacities, from gelling agents in food, to pharmaceuticals and health aids, to photography, cosmetic manufacturing, and adhesives. Within the health industry, collagen preparations have been used to enhance athletic performance by supplying essential amino acids and shortening recovery time after exercise, and have also been used as weight loss aids and digestive aids as well as to relieve pain, reduce inflammation, and improve joint function for patients with osteoarthritis and rheumatoid arthritis. Collagen preparations have been used as supplements to combat osteoporosis and improve the condition of fingernails and hair. In the cosmetic industry, meanwhile, collagen preparations are available as topical products for use on the skin to increase skin suppleness, reduce the appearance of wrinkles and fine lines, and to reduce the appearance of stretch marks.

Although the raw materials for extracting collagen are readily available as byproducts from other industries, such as the fishing and poultry processing industries, current methods for producing collagen are expensive and time-consuming. Cartilage tissue must be separated from meat and bones and chopped. Following extraction, a number of purification steps are often required, including the use of decolorizing agents, antibacterial and antifungal agents, and the like. Product odor is also a consideration; collagen preparations with strong odors will be unsuitable, especially for incorporation into cosmetic or food products. This is a particular issue with undenatured collagen preparations but can be a problem with any collagen preparation.

It would thus be advantageous to have a fast and efficient process for producing collagen preparations containing primarily undenatured collagen. It would further be advantageous if this process resulted in the production of collagen of high purity with little to no discoloration and odor.

SUMMARY

Disclosed herein are methods for efficiently isolating collagen form a collagen source. The methods are inexpensive and do not require the use of proteolytic enzymes, decolorizing agents, antibacterial and antifungal agents, and the like. Further, the collagen produced by the methods described herein is substantially free of odor and discoloration. Still further, the collagen produced by the methods described herein is suitable to be used in cosmetics, food products, and pharmaceuticals or nutritional supplements.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Before the present compounds, compositions, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "an enzyme" includes mixtures of two or more such enzymes, and the like.

"Optional" or "optionally" means that the subsequently-described event or circumstance can or cannot occur, and that the description includes instances where the event or circumstance occurs and instances where it does not.

As used herein, "cartilage" refers to a type of connective tissue in animals. It is a flexible tissue that is somewhat more rigid than muscle and is found in various locations throughout the body including joints, the rib cage, the nose and ear, bronchial tubes, the trachea, between the vertebrae, and so forth. Cartilage tissue contains a large amount of extracellular matrix that is high in collagen and other proteoglycans. Chondrocytes are matrix-producing cells that have become trapped in the matrix.

"Collagen" is a structural protein found in connective tissue; it frequently takes the form of fibrils arranged in a triple helix. Fibrillar types of collagen include Types I, II, III, V, and XI. Type I collagen makes up a great deal of the organic part of bone as well as being found in skin, tendons, blood vessels, and organs, while type III collagen is commonly found near or with type I. On the other hand, cartilage is composed primarily of type II collagen. Other types of collagen are less common and may be found in membranes, on cell surfaces, and associated with hair or placental structures.

As used herein, "undenatured" collagen is collagen that retains its original molecular weight and amino acid sequence and optionally its original three-dimensional (tertiary) structure. Undenatured collagen has not been hydrolyzed into its component amino acids and may or may not be associated with proteoglycans or carbohydrate polymers such as, for example, chondroitin sulfate or hyaluronic acid, that are also typically found in cartilage. "Undenatured" collagen may sometimes be referred to as "native" collagen, referring to the fact that undenatured proteins retain their native folds.

In one aspect, telopeptides are removed from the collagen using the methods described herein. "Telopeptide" as used herein refers to an amino acid sequence at the N-terminus or C-terminus of a protein that has a function during protein synthesis or folding but that may be removed at maturity or that can be removed in an enzymatic process in vitro.

The sternum, or breastbone, is a large bone to which the pectoral muscles are attached. In avians such as chickens, ducks, turkeys, and other poultry, the sternum is positioned under the body and is enlarged in size for attachment of powerful flight muscles. Avian sterna are typically associated with a large proportion of cartilage that is rich in type II collagen.

As used herein, "neutralization" refers to the treatment of an acidic reaction solution with an approximately quantitative amount of a base, or to the reverse, that is, treatment of an alkaline reaction solution with an approximately quantitative amount of an acid. "Neutralization" can also refer to treatment of an enzymatic reaction solution with acid, base, or extreme hot or cold temperature to denature the enzyme and stop the enzymatic reaction.

An "anti-bacterial agent" is any compound or composition or treatment that destroys bacteria. Alternatively, an anti-bacterial agent can suppress the growth of bacteria or can prevent bacteria from reproducing. Ultraviolet light, heat treatment, certain chemicals such as bleach or ethanol, and antibiotics are considered anti-bacterial.

As used herein, the term "about" is used to provide flexibility to a numerical range endpoint by providing that a given value may be "a little above" or "a little below" the endpoint without affecting the desired result.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also to include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the list solely based on their presentation in a common group without indications to the contrary.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference of each various individual and collective combination and permutation of these compounds may not be explicitly disclosed, each is specifically contemplated and described herein. For example, if a digestive enzyme is disclosed and a number of different acids intended for bringing a solution to optimum pH for the digestive enzyme's action are discussed, each and every combination and permutation of enzyme and acid that is possible is specifically contemplated unless specifically indicated to the contrary. For example, if a class of molecules A, B, and C are disclosed, as well as a class of molecules D, E, and F, and an example of a combination A+D is disclosed, then even if each is not individually recited, each is individually and collectively contemplated. Thus, in this example, each of the combinations A+E, A+F, B+D, B+E, B+F, C+D, C+E, and C+F, are specifically contemplated and should be considered disclosed from disclosure of A, B, and C; D, E, and F; and the example combination of A+D. Likewise, any subset or combination of these is also specifically contemplated and disclosed. Thus, for example, the sub-group of A+E, +F, and C+E is specifically contemplated and should be considered disclosed from disclosure of A, B, and C; D, E, and F; and the example combination of A+D. This concept applies to all aspects of this disclosure including, but not limited to, steps in methods of making and using the disclosed compositions. Thus, if there exist a variety of additional steps that can be performed with any specific embodiment or combination of embodiments of the disclosed methods, each such combination is specifically contemplated and should be considered disclosed.

References in the specification and concluding claims to parts by weight of a particular element or component denote the weight relationship between the element or component and any other elements or components in the compound or composition for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Described herein are methods for isolating collagen a collagen source. In one aspect, the source of the collagen is an avian sternum such as, for example, a chicken, turkey, or duck sternum. In another aspect, the collagen source is chicken sternum. In a further aspect, the avian sternum primarily contains type II collagen and the collagen isolated is a type II collagen. The sternum is the largest cartilage-containing object in the chicken skeleton. In one aspect, the sternum is removed from the avian skeleton manually using, for example, kitchen shears. In another aspect, the sternum is removed mechanically. In an alternative aspect, the sternum is not removed from the skeleton.

In another aspect, when the collagen source is an avian sternum such as chicken sternum, the chicken sternum can be used immediately. In an alternative aspect, the chicken sternum can be treated with an anti-bacterial agent prior to employing the process described herein. The anti-bacterial agent can be any composition or method known to kill or prevent the growth of bacteria such as, for example, heat treatment, ultraviolet irradiation, a substance such as bleach or ethanol, or an antibiotic. In one aspect, the anti-bacterial agent is ethanol. Further in this aspect, the chicken sternum is stored in enough ethanol to cover the collagen source. The ethanol can be from 60% to 100% ethanol, or can be 60%, 70%, 80%, 90%, or 100% ethanol, where any value can be a lower- or upper-endpoint of a range (e.g., 60% to 80%). In one aspect, the ethanol is 70% ethanol. In a related aspect, the use of ethanol is a safety measure to prevent bacterial contamination of the resulting product. In one aspect, the chicken sternum is stored in the anti-bacterial agent prior to use.

In one aspect, when it is time to process the avian sternal cartilage, a volume of aqueous ethanol is added to the cartilage. In one aspect, the aqueous ethanol is from 5:95%

(v/v) to 40:60% (v/v) ethanol/water. In another aspect, the aqueous ethanol is 10, 20, 30, 40, 45, 50, 55, 60, or 70% ethanol (v/v) with the remainder being water, where any value can be a lower- or upper-endpoint of a range (e.g., 10% to 30%).

In one aspect, the volume of aqueous ethanol is from 1 to 10 mL per gram of cartilage. In another aspect, the volume can be 1, 2, 3, 4, 5, 6, 7, 8, 9, or 10 mL per gram of cartilage, where any value can be a lower- or upper-endpoint of a range (e.g., 1 mL to 3 mL). In one aspect, 2 mL of a 20% ethanol:80% water solution is added per gram of collagen source. Further in this aspect, the collagen source is homogenized with the aqueous ethanol. Homogenization can be accomplished with the use of a blender or other homogenizers used in the art. Further in this aspect, the blender can be a commercial blender or a blender intended for home use. In one aspect, homogenization is performed at the blender's maximum speed. In a further aspect, homogenization is carried out for from 5 to 15 minutes or for 5, 6, 7, 8, 9, 10, 11, 12, 13, 14, or 15 minutes. In one aspect, homogenization is carried out for 10 minutes. Not wishing to be bound by theory, use of the blender disrupts the cartilage and increases the exposed surface area of tissue. Further in this aspect, increased surface area allows subsequent reactions to proceed more efficiently. In still another aspect, the 20% ethanol removes fat and/or additional contaminating material from the cartilage preparation.

In one aspect, following homogenization, the cartilage composition is stirred with aqueous ethanol for 12 to 48 hours, or for 12, 24, 36, or 48 hours, where any value can be a lower- or upper-endpoint of a range (e.g., 12 hours to 36 hours). In one aspect, stirring is carried out for 24 hours. In a further aspect, following homogenization, the resulting solution is centrifuged (i.e., first centrifugation step). In one aspect, first centrifugation is carried out at from 4 to 30° C. or at 4, 5, 6, 7, 8, 9, 10, 12, 15, 20, 25, or 30° C. In one aspect, first centrifugation is carried out at 4° C. In a further aspect, first centrifugation is carried out at a force of from 5,000 to 15,000×g or is carried out at 5,000; 6,000; 7,000; 8,000; 9,000; 10,000; 11,000; 12,000; 13,000; 14,000; or 15,000×g. In one aspect, first centrifugation is performed at 10,000×g. In still another aspect, first centrifugation is carried out for from 5 to 40 minutes or is carried out for 5, 10, 15, 20, 25, 30, 35, or 40 minutes. In another aspect, centrifugation is carried out for 20 minutes.

After the first centrifugation step, the supernatant liquid is discarded after centrifugation. In another aspect, the first centrifugation step is repeated. Not wishing to be bound by theory, first centrifugation accomplishes the separation of the denser, insoluble cartilage from solubilized impurities. In a still further aspect, contaminants that are soluble in aqueous ethanol are removed with the supernatant when it is discarded. Further in this aspect, the lower layer can be a pellet or can be a gel-like material. In one aspect, the lower, non-supernatant layer is a gel-like material.

In a further aspect, after first centrifugation, an aqueous solution of a base is added in an amount sufficient to cover the collagen source. In one aspect, the base is an alkali base or alkaline earth metal base. In a further aspect, the base is an alkali hydroxide. In an alternative aspect, the base is sodium hydroxide, sodium hydrogen carbonate, sodium bicarbonate, or potassium hydroxide. In one aspect, the aqueous base is sodium hydroxide having a concentration of from 0.05 to 0.5 M, or is 0.05, 0.1, 0.2, 0.3, 0.4, or 0.5 M, where any value can be a lower- or upper-endpoint of a range (e.g., 0.1 M to 0.3 M). In a further aspect, the sodium hydroxide concentration is 0.2 M. In another aspect, the amount of aqueous sodium hydroxide is sufficient to cover the cartilage. In still another aspect, the volume of aqueous base is from about 1 mL per gram of wet cartilage to about 5 mL per gram of wet cartilage, or is 1, 2, 3, 4, or 5 mL per gram of wet cartilage starting weight, where any value can be a lower- or upper-endpoint of a range (e.g., 1 mL to 3 mL per gram of wet cartilage). In one aspect, the volume of aqueous base (e.g., sodium hydroxide) is 2 mL per gram of wet cartilage.

In one aspect, the ratio of collagen source to moles of base is from 500 g cartilage/mole of base to 5,000 g cartilage/mole of base. In another aspect, the ratio of avian sternal cartilage is 500, 750, 1000, 2000, 2500, 3000, 4000, or 5000 grams of cartilage per mole of base, where any value can be a lower- or upper-endpoint of a range (e.g., 500 to 1,000 grams of cartilage per mole of base).

Following the addition of aqueous base, the resulting solution is stirred for from 12 to 48 hours, or is stirred for 12, 24, 36, or 48 hours. In one aspect, the stirring is carried out for 24 hours. In one aspect, stirring in aqueous NaOH solution can help remove contaminants from the collagen preparation.

In a further aspect, following stirring in aqueous base, the resulting solution can be centrifuged (i.e., second centrifugation step). In one aspect, second centrifugation is carried out at from 4 to 30° C. or at 4, 5, 6, 7, 8, 9, 10, 12, 15, 20, 25, or 30° C. In one aspect, second centrifugation is carried out at 4° C. In a further aspect, second centrifugation is carried out at a force of from 5,000 to 15,000×g or is carried out at 5,000; 6,000; 7,000; 8,000; 9,000; 10,000; 11,000; 12,000; 13,000; 14,000; or 15,000×g. In one aspect, second centrifugation is performed at 10,000×g. In still another aspect, second centrifugation is carried out for from 5 to 40 minutes or is carried out for 5, 10, 15, 20, 25, 30, 35, or 40 minutes. In another aspect, second centrifugation is carried out for 20 minutes. In one aspect, the supernatant is discarded after second centrifugation. Not wishing to be bound by theory, discarding the supernatant accomplishes removal of contaminants that dissolve in mildly basic solutions. Additionally, after the second centrifugation step, relatively small amounts of solid material have been removed. Further in this aspect, weighing the solid remaining after centrifugation shows a loss of mass ranging from 1 to 20% relative to the original starting weight of the cartilage, or a loss of mass that is about 1, 2, 3, 4, 5, 6, 7, 8, 9, 10, 11, 12, 15, or 20% relative to the original starting weight of the cartilage. Still further in this aspect, the loss of mass is from 5% to 10%.

Following second centrifugation and isolation of the resulting precipitate, the precipitate is contacted with a digestive enzyme. In one aspect, the digestive enzyme is α-galactosidase, cellulase, glycoamylase, invertase, lactase, maltase, isomaltase, malt diastase, protease, peptidase, papain, bromelain, aminopeptidase, carboxypeptidase, chymotrypsin, deoxyribonuclease, dipeptidase, elastase, enterokinase, ptyalin, gelatinase, rennin, betaine, gastric lipase, lactase, lingual lipase, maltase, a nucleosidase, phospholipase, elastase, a phosphatase, pancreatic amylase, pancreatic lipase, pepsin, ribonuclease, sucrase, salivary amylase, trypsin, or α-dextrinase. In a further aspect, the digestive enzyme is pepsin.

In a further aspect, the digestive enzyme is used as a powder. In an alternative aspect, the digestive enzyme is used as a solution. In any aspect, the digestive enzyme is provided in an amount of from 1% to 10% (w/w) of the total collagen source (wet or dry) used in the beginning of the process. In one aspect, the amount of the digestive enzyme used is 0.01, 0.05, 0.1, 0.25, 0.5, 0.75, 1, 2, 3, 4, 5, 6, 7, 8, 9, or 10% (w/w), where any value can be a lower- or upper-endpoint of a range (e.g., 3% to 7%). In one aspect, the digestive enzyme is provided at 5% (w/w).

In a further aspect, the collagen source (e.g., precipitate produced from second centrifugation) is contacted with a digestive enzyme and an aqueous acid. In one aspect, the aqueous acid is acetic acid, citric acid, lactic acid, hydrochloric acid, formic acid, nitric acid, sulfuric acid, or phosphoric acid. In a further aspect, the aqueous acid is acetic acid. In a further aspect, aqueous acetic acid is added sequentially or concurrently with the digestive enzyme to the collagen source as separate components. Alternatively, the digestive enzyme and aqueous acid can be premixed then subsequently added to the collagen source. In one aspect, from 5 to 20 mL of aqueous acetic acid per gram of collagen source is used, or 5, 10, 15, or 20 mL per gram of collagen source is used. In one aspect, 10 mL of aqueous acetic acid per gram of collagen source is used. In a further aspect, the aqueous acetic acid is present at a concentration of from 0.1 to 2 M, or is present at 0.1, 0.2, 0.3, 0.4, 0.5, 0.6, 0.7, 0.8, 0.9, 1, 1.25, 1.5, 1.75, or 2 M,) where any value can be a lower- or upper-endpoint of a range (e.g., 0.1 M to 1 M). In one aspect, the acetic acid is 0.5 M.

Following addition of the digestive enzyme and aqueous acid to the collagen source, the composition is incubated with shaking at a temperature of from 20 to 40° C. In one aspect, incubation is accomplished at 20, 22, 25, 30, 35, 37, or 40° C. Further in this aspect, the incubation is accomplished at the optimum temperature for operation of the digestive enzyme. In one aspect, when the digestive enzyme is pepsin, incubation is carried out at 30° C. In a further aspect, incubation is carried out for from 24 to 72 hours, or is carried out for 24, 48, or 72 hours. In one aspect, incubation lasts for 48 hours.

Not wishing to be bound by theory, treatment with a digestive enzyme removes telopeptides from collagen. Further in this aspect, removal of telopeptides allows the resulting collagen to become soluble in water. In another aspect, treatment with a digestive enzyme removes contaminating proteins. In still another aspect, treatment with a digestive enzyme does not hydrolyze the collagen.

In one aspect, following incubation with a digestive enzyme, the collagen preparation is centrifuged (i.e., third centrifugation step). In one aspect, third centrifugation is carried out at from 4 to 30° C. or at 4, 5, 10, 15, 20, 25, or 30° C. In one aspect, centrifugation is carried out at 20° C. In a further aspect, third centrifugation is carried out at a force of from 5,000 to 15,000×g or is carried out at 5,000; 6,000; 7,000; 8,000; 9,000; 10,000; 11,000; 12,000; 13,000; 14,000; or 15,000×g. In one aspect, third centrifugation is performed at 12,000×g. In still another aspect, third centrifugation is carried out from 15 to 60 minutes or is carried out for 15, 20, 25, 30, 35, 40, 45, 50, 55, or 60 minutes. In another aspect, third centrifugation is carried out for 40 minutes.

In one aspect, the pellet is discarded after third centrifugation and the pH of the resulting supernatant is adjusted in order to deactivate the digestive enzyme. In one aspect, the pH of the supernatant solution is adjusted from 6.5 to 11.0 or is adjusted to 6.5, 7, 7.5, 8, 8.5, 9, 9.5, 10, 10.5, or 11, where any value can be a lower- or upper-endpoint of a range (e.g., 6.5 to 8). In one aspect, the pH is adjusted using an aqueous solution of a base. In one aspect, the base is an alkali base. In one aspect, the base is sodium hydroxide, potassium hydroxide, sodium hydrogen carbonate, or sodium carbonate. In a further aspect, the base is sodium hydroxide. In one aspect, the base is present at a concentration of from 0.5 to 2 M, or is present at 0.5, 1, 1.5, or 2M, or is 1 M. Alternatively, the digestive enzyme can be deactivated by heat treatment or another treatment as indicated by the supplier. In one aspect, the solution of supernatant and aqueous base is incubated with shaking. In one aspect, incubation is carried out for from 12 to 48 hours, or is carried out for 12, 24, 36, or 48 hours. In another aspect, incubation is conducted for 24 hours. In a further aspect, incubation is conducted at a temperature ranging from 10 to 50° C. or is conducted at 10, 20, 30, 40, or 50° C. In a further aspect, incubation is conducted at 30° C.

Following incubation with base to deactivate the digestive enzyme, the pH of the solution can be adjusted again. In one aspect, the pH is adjusted to a value lower than 5.0. In one aspect, the pH decrease is accomplished by addition of an acid to the solution produced above. In this aspect, the acid can be acetic acid, citric acid, lactic acid, formic acid, hydrochloric acid, phosphoric acid, nitric acid, or sulfuric acid. In one aspect, the acid is acetic acid. In a further aspect, the acid solution that is added is from 1 to 10 M, or is 1, 2, 3, 4, 5, 6, 7, 8, 9, or 10 M, where any value can be a lower- or upper-endpoint of a range (e.g., 4 M to 8 M). In one aspect, the acid solution is 6 M.

In one aspect, after reducing the pH of the solution, a salt is added to the solution. In one aspect, the salt is sodium chloride, potassium chloride, potassium iodide, or a mixture thereof. In another aspect, the salt is sodium chloride. Not wishing to be bound by theory, the addition of the salt to the solution precipitates the collagen while contaminants remain in solution. In one aspect, the salt is added to the reaction mixture such that the concentration of the salt in the solution is from 0.25 to 3 M, or is 0.25, 0.5, 0.75, 1, 1.5, 2, 2.5, or 3M, where any value can be a lower- or upper-endpoint of a range (e.g., 0.5 M to 2 M). In another aspect, the salt is added prior to the addition of acid used to reduce the pH of the solution. Alternatively, the acid and salt are added concurrently. In one aspect, the acid is acetic acid and the salt is sodium chloride and the acetic acid is added sequentially before the sodium chloride.

In another aspect, following salt precipitation, the collagen preparation is centrifuged (i.e., fourth centrifugation step). In one aspect, fourth centrifugation is carried out at from 4 to 30° C. or at 4, 5, 10, 15, 20, 25, or 30° C. In one aspect, fourth centrifugation is carried out at 20° C. In a further aspect, fourth centrifugation is carried out at a force of from 5,000 to 15,000×g or is carried out at 5,000; 6,000; 7,000; 8,000; 9,000; 10,000; 11,000; 12,000; 13,000; 14,000; or 15,000×g. In one aspect, fourth centrifugation is performed at 12,000×g. In still another aspect, fourth centrifugation is carried out for from 15 to 60 minutes or is carried out for 15, 20, 25, 30, 35, 40, 45, 50, 55, or 60 minutes. In another aspect, fourth centrifugation is carried out for 40 minutes.

Following fourth centrifugation, the supernatant is discarded the precipitate (e.g., pellet). In one aspect, the collagen pellet can be dissolved in an aqueous acid solution. In one aspect, the acid is acetic acid, citric acid, lactic acid, formic acid, hydrochloric acid, phosphoric acid, nitric acid, or sulfuric acid. In a further aspect, the acid is acetic acid. In one aspect, the acid is present in a concentration of from 0.1 to 1 M, or is present at 0.1, 0.2, 0.3, 0.4, 0.5, 0.6, 0.7, 0.8, 0.9, or 1 M, where any value can be a lower- or upper-endpoint of a range (e.g., 0.1 M to 1 M). In another aspect, the acid is 0.5 M in concentration. In one aspect, the acid is added at a proportion of from 10 to 50 mL per gram of collagen pellet, or is 10, 20, 30, 40, or 50 mL per gram of collagen, where any value can be a lower- or upper-endpoint of a range (e.g., 10 to 20 mL per gram of collagen). In an alternative aspect, the acid is added at a proportion of 20 mL per gram of collagen pellet. In one aspect, the time and amount of acid used is sufficient to dissolve the collagen. In one aspect, the dissolution of the collagen takes from 3 to 10 hours, or takes 3, 4, 5, 6, 7, 8, 9, or 10 hours. In one aspect, dissolution takes about 6 hours. In another aspect, the rate of dissolution can be increased with stirring, shaking, or gentle heating.

Following dissolution of the collagen pellet, the collagen solution can be dialyzed against deionized water. Not wishing to be bound by theory, dialysis removes small molecular weight contaminants, salts, acid residue, and the like. Here, the dialysis cartridge or tubing allows small molecules to cross a membrane along their concentration gradient while retaining large molecules such as collagen. In one aspect, if any collagen precipitates during dialysis, it can be resuspended by simple mixing. In one aspect, dialysis membranes with a molecular weight cut off (MWCO) of from 5,000 Da to 10,000 Da are used. In a further aspect, the MWCO of the dialysis membranes is from 6,000 to 8,000 Da.

Following dialysis, the collagen solution can be dried in several ways. In one aspect, the collagen solution is frozen and then lyophilized. In one aspect, lyophilization results in a solid powder with no volatile contaminants such as acetic acid or other small, volatile organic acids. In one aspect, the solution can be frozen rapidly in liquid nitrogen, resulting in a dense solid, or can be slowly frozen in a −20 or −80° C. freezer and then lyophilized, resulting in a fluffier solid. In an alternative aspect, the collagen solution is spray-dried.

In one aspect, the yield from the above procedure is about 1 gram of purified collagen powder per 100 grams of collagen source (e.g., chicken sternum). In another aspect, the final product is a white solid. In still another aspect, the final product does not need to be decolorized with charcoal or by another method prior to use. In still another aspect, the final product is odorless. In one aspect, about 10 mg of the final product will dissolve in about 15 mL of 0.15 M acetic acid.

The type and purity of the collagen produced by the process herein can be evaluated using techniques known in the art. In one aspect, gel electrophoresis can be used. In addition to gel electrophoresis, the collagen produced by the process described herein can be characterized by ELISA. For example, ELISA kits manufactured by Astarte Biologics (Rheumera®) and Chondrex (hydroxyproline assay kit) can be used to evaluate the content and purity of the collagen produced herein. In one aspect, the collagen produced herein has a total collagen content of greater than 60%, greater than 70%, greater than 80%, greater than 90%, or greater than 95% by weight. In another aspect, the collagen produced herein is type II collagen greater than 30%, greater than 40%, greater than 50%, greater than 60%, greater than 70%, greater than 80%, greater than 90%, or greater than 95% by weight of the total amount of collagen produced. In another aspect, collagen produced herein has a protein content of greater than 50%, greater than 60%, greater than 70%, greater than 80%, greater than 90%, greater than 95%, greater than 99%, or 100%.

In one aspect, the final product is substantially free of denatured collagen. In an alternative aspect, the final product contains a small amount of denatured collagen in addition to collagen in native form. In one aspect, the collagen is type II collagen that is 80% to 100% undenatured, or is at least 80%, 90%, 95%, 99%, or 100% undenatured.

The collagen produced herein is also an indicator of the type and purity of the collagen. In one aspect, the collagen produced herein is completely soluble in aqueous acid. For example, 10 mg of collagen produced herein is soluble 15 mL of 0.15 M acetic acid at 4° C.

In one aspect, provided herein is a method for isolating collagen comprising
(a) contacting the collagen source with an aqueous base to produce a first composition comprising a first supernatant and a first precipitate;
(b) separating the first precipitate from the first supernatant;
(c) contacting the first precipitate with a digestive enzyme to produce a second composition comprising a second supernatant and a second precipitate;
(d) separating the second supernatant from the second precipitate;
(e) deactivating the digestion enzyme in the second supernatant to produce a third composition;
(f) precipitating the collagen from the third composition;
(g) separating the collagen from the third composition; and
(h) purifying the collagen by dialysis and subsequent lyophilization.

In another aspect, provided herein is a method for isolating collagen from chicken sternum comprising
(a) contacting the chicken sternum with aqueous sodium hydroxide to produce a first composition comprising a first supernatant and a first precipitate, wherein the ratio of chicken sternum per mole of sodium hydroxide is from 500 g chicken sternum/mole of base to 5,000 g chicken sternum/mole of base;
(b) separating the first precipitate from the first supernatant;
(c) contacting the first precipitate with a digestive enzyme and an aqueous acid to produce a second composition comprising a second supernatant and a second precipitate, wherein the digestive enzyme is pepsin in the amount of 1% to 10% w/w per the collagen source and the aqueous acid is acetic acid having a concentration of from 0.1 M to 2 M;
(d) separating the second supernatant from the second precipitate;
(e) deactivating the digestion enzyme in the second supernatant comprising adjusting the pH of the second supernatant to a pH greater than 7.0 but less than or equal to 11 to produce a third composition;
(f) precipitating the collagen from the third composition comprising (1) adjusting the pH of the third composition to a pH of less than 5.0 by adding an acid to the third composition and (2) adding a salt to the third composition;
(g) separating the collagen from the third composition; and
(h) purifying the collagen by dialysis and subsequent lyophilization.

EXAMPLES

The following examples are put forth so as to provide those of ordinary skill in the art with a complete disclosure and description of how the compounds, compositions, and methods described and claimed herein are made and evaluated. The examples are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions, e.g., component concentrations, desired solvents, solvent mixtures, temperatures, pressures, and other reaction ranges and conditions can be used to optimize the product purity and yield obtained from the described process. Only reasonable and routine experimentation will be required to optimize such processes and conditions.

Example 1: Ratio of Amount of Chicken Sternum to Moles of Base

In a general procedure to prepare collagen, the amount of cartilage treated with sodium hydroxide was 5 g per 2 mL of base. The following calculation was used to determine the amount of chicken sternum per mole of base:

Moles of NaOH in 2 mL of 0.2M solution:

$$\frac{0.2 \text{ moles NaOH}}{1 \text{ L}} \times \frac{1 \text{ L}}{1000 \text{ mL}} \times 2 \text{ mL} = 0.0004 \text{ moles NaOH}$$

Ratio of 5 grams of chicken sternum treated with 2 mL of 0.2 M NaOH (i.e., 0.0004 moles of NaOH):

$$\frac{1 \text{ g chicken sternum}}{0.0004 \text{ moles NaOH}} = \frac{2500 \text{ g chicken sternum}}{\text{mol NaOH}}$$

Thus, when 1 gram of chicken sternal cartilage is treated with 2 mL of 0.2M NaOH, this is equivalent to 2,500 grams of chicken sternal cartilage being treated with 1 mole of aqueous NaOH.

Example 2: Procedure for Preparation of Collagen

The following general procedure was used to prepare substantially undenatured collagen from chicken sternal cartilage. Some parameters were varied during the course of optimization of conditions.

(1) Sternal cartilage was removed from chicken skeleton. Cartilage was either used immediately or stored in a volume of 70% ethanol sufficient to cover the biological material.

(2) 2 mL of 20% ethanol: 80% water were added per gram of cartilage. The mixture was homogenized in a blender for 10 minutes at maximum speed, followed by stirring the solution in 20% ethanol for 24 hours.

(3) The solution was centrifuged at 10,000×g for 20 minutes at 4° C. and the supernatant was discarded.

(4) The solution was again centrifuged at 10,000×g for 20 minutes and the supernatant was discarded. Optionally, only one centrifugation step is used for 20 minutes or for a longer time.

(5) 0.2 M aqueous NaOH was added to the solution in an amount sufficient to cover the cartilage. This was equal to approximately 2 mL of NaOH solution per gram of wet cartilage starting weight. The solution was stirred for 24 hours.

(6) The solution was centrifuged at 10,000×g for 20 minutes at 4° C. and the supernatant was discarded.

(7) 5% w/w pepsin and 10 volumes 0.5 M aqueous acetic acid were added to the pellet/precipitate. This solution was incubated with shaking for 48 hours at 30° C.

(8) The solution was then centrifuged at 12,000×g for 40 minutes at 20° C. and the pellet was discarded.

(9) Supernatant pH was adjusted to a value greater than 7.0 but less than 11 using 1M NaOH. This solution was incubated with shaking for 24 hours at 30° C.

(10) The solution pH was then adjusted to a value lower than 4.5 using 6M acetic acid. Sodium chloride was then added to a final concentration of 1 M and the solution was centrifuged at 12,000×g for 40 minutes at 20° C. and the supernatant was discarded.

(11) The pellet was dissolved in 0.5 M aqueous acetic acid (20 mL aqueous acetic acid per gram of pellet) and dialyzed against deionized water in celluloid dialysis tubing with 6,000 to 8,000 a molecular weight cut-off limit.

(12) The collagen solution was frozen and the water was removed via lyophilization (freeze drying). Alternatively, the collagen solution is dried using a spray-drying technique.

This method yielded about 1 gram of purified collagen powder from approximately 100 grams of cartilage.

Example 3: Characterization of Collagen Product

The final product is a solid white material, about 10 mg of which will dissolve in 15 mL of 0.15 M aqueous acetic acid.

Denaturing polyacrylamide gel electrophoresis (PAGE) was used to determine approximate molecular weight. A combination of sodium dodecyl sulfate (SDS) and heat served as denaturant. Separated proteins were visualized using Coomassie blue stain.

When prepared according to the procedure in Example 1, approximately 90% of the protein had an apparent molecular mass of approximately 110 kDA and 10% had an apparent molecular mass of approximately 220 kDa as determined by gel electrophoresis, which is consistent with the presence of type II collagen. Trace amounts of protein having molecular weights 100 kDA and 65 kDA were also evident. Molecules with molecular weights under 5 kDA (e.g., amino acids, small peptides, and salts) were unlikely to be present due to the process outlined in Example 1. 10 mg of the collagen product was soluble in 15 mL of 0.15 M acetic acid at 4° C. The collagen product had a protein content at or near 100%, and the total collagen content was greater than 95%.

Throughout this publication, various publications are referenced. The disclosures of these publications in their entireties are hereby incorporated by reference into this application in order to more fully describe the methods, compositions, and compounds herein.

Various modifications and variations can be made to the methods, compositions, and compounds described herein. Other aspects of the methods, compositions, and compounds will be apparent from consideration of the specification and practice of the methods, compositions, and compounds disclosed herein. It is intended that the specification and examples be considered as exemplary.

What is claimed:

1. A method for isolating collagen from a collagen source, the method comprising
   (a) contacting the collagen source with an aqueous base to produce a first composition comprising a first supernatant and a first precipitate, wherein the aqueous base comprises an alkali base or an alkaline earth metal base, wherein the alkali base or the alkaline earth metal base has a concentration of 0.05M to 0.5M;
   (b) separating the first precipitate from the first supernatant;
   (c) contacting the first precipitate with a digestive enzyme at a temperature greater than or equal to 25° C. to produce a second composition comprising a second supernatant and a second precipitate, wherein the digestive enzyme comprises protease, papain, bromelain, chymotrypsin, rennin, elastase, pancreatic amylase, pancreatic lipase, pepsin, trypsin, or any combination thereof;

(d) separating the second supernatant from the second precipitate;

(e) deactivating the digestion enzyme in the second supernatant comprising adjusting the pH of the second supernatant to a pH greater than 7.0 but less than or equal to 11 to produce a third composition;

(f) precipitating the collagen from the third composition; and (g) separating the precipitated collagen from the third composition.

2. The method of claim 1, wherein the collagen source comprises avian sternum.

3. The method of claim 1, wherein the collagen source comprises chicken sternum.

4. The method of claim 1, wherein the collagen source is chicken sternum, and the chicken sternum is removed from the chicken skeleton prior to step (a).

5. The method of claim 4, wherein the chicken sternum is homogenized in aqueous ethanol.

6. The method of claim 4, wherein the aqueous ethanol is 5:95 vol % to 40:60 vol % mixture of ethanol and water.

7. The method of claim 1, wherein the aqueous base comprises an alkali hydroxide.

8. The method of claim 1, wherein the aqueous base is sodium hydroxide.

9. The method of claim 1, wherein the ratio of chicken sternum per mole of base is from 500 g chicken sternum/mole of base to 5,000 g chicken sternum/mole of base.

10. The method of claim 1, wherein, wherein step (a) is conducted at a temperature of from 4° C. to 30° C. for 0.5 hours to 48 hours.

11. The method of claim 1, wherein the digestive enzyme comprises pepsin.

12. The method of claim 1, wherein the digestive enzyme comprises pepsin in the amount of 1% to 10% w/w per the collagen source.

13. The method of claim 1, wherein in step (c) the first precipitate is further contacted with an acid.

14. The method of claim 12, wherein the aqueous acid comprises acetic acid, citric acid, lactic acid, hydrochloric acid, formic acid, nitric acid, sulfuric acid, phosphoric acid, or any combination thereof.

15. The method of claim 12, wherein the aqueous acid comprises acetic acid having a concentration of from 0.1 M to 2 M.

16. The method of claim 1, wherein step (c) is conducted at a temperature of from 25° C. to 40° C.

17. The method of claim 1, wherein step (e) comprises admixing a base with the second supernatant at a temperature of from 20° C. to 40° C. for a period of 0.5 hours to 48 hours.

18. The method of claim 17, wherein the base is an alkali base.

19. The method of claim 17, wherein the base is sodium hydroxide at a concentration of from 0.1 M to 2 M.

20. The method of claim 1, wherein step (f) comprises (1) adjusting the pH of the third composition to a pH of less than 5.0 by adding an acid to the third composition and (2) adding a salt to the third composition.

21. The method of claim 20, wherein the acid comprises acetic acid, citric acid, lactic acid, hydrochloric acid, formic acid, nitric acid, sulfuric acid, phosphoric acid, or any combination thereof.

22. The method of claim 20, wherein the acid comprises acetic acid.

23. The method of claim 22, wherein the acetic acid has a concentration of from 1 M to 10 M.

24. The method of claim 20, wherein the salt is added to the third composition so that the concentration of the salt is from 0.5 M to 2 M.

25. The method of claim 20, wherein the salt comprises sodium chloride, potassium chloride, potassium iodide, or any combination thereof.

26. The method of claim 20, wherein the salt comprises sodium chloride.

27. The method of claim 20, wherein the acid comprises acetic acid and the salt comprises sodium chloride, wherein the acetic acid is admixed with the third composition followed by admixing with sodium chloride.

28. The method of claim 1, wherein after step (g), (1) dissolving the collagen in an aqueous acid to produce a collagen solution, (2) dialyzing the collagen solution in deionized water, and (3) removing water from the collagen solution to produce collagen as a dry powder.

29. The method of claim 28, wherein the acid comprises acetic acid, citric acid, lactic acid, hydrochloric acid, formic acid, nitric acid, sulfuric acid, phosphoric acid, or any combination thereof.

30. The method of claim 28, wherein the acid comprises acetic acid.

31. The method of claim 28, wherein the acid comprises acetic acid at a concentration of from 0.1 M to 2 M and the collagen solution is dialyzed against deionized water.

32. The method of claim 28, wherein the water is removed by lyophilization.

33. A method for isolating collagen from chicken sternum, the method comprising (a) contacting the chicken sternum with aqueous sodium hydroxide to produce a first composition comprising a first supernatant and a first precipitate, wherein the ratio of chicken sternum per mole of sodium hydroxide is from 500 g chicken sternum/mole of base to 5,000 g chicken sternum/mole of base;

(b) separating the first precipitate from the first supernatant;

(c) contacting the first precipitate with a digestive enzyme and an aqueous acid at a temperature of greater than or equal to 25° C. to produce a second composition comprising a second supernatant and a second precipitate, wherein the digestive enzyme is pepsin in the amount of 1% to 10% w/w per the collagen source and the aqueous acid is acetic acid having a concentration of from 0.1 M to 2 M;

(d) separating the second supernatant from the second precipitate;

(e) deactivating the digestion enzyme in the second supernatant comprising adjusting the pH of the second supernatant to a pH greater than 7.0 but less than or equal to 11 to produce a third composition;

(f) precipitating the collagen from the third composition comprising (1) adjusting the pH of the third composition to a pH of less than 5.0 by adding an acid to the third composition and (2) adding a salt to the third composition; and (g) separating the collagen from the third composition.

34. The method of claim 33, wherein in step (f) the acid is acetic acid and the salt is sodium chloride, wherein the acetic acid is admixed with the third composition followed by admixing with sodium chloride.

35. The method of claim 33, wherein after step (g), (1) dissolving the collagen in an aqueous acid to produce a collagen solution, (2) dialyzing the collagen solution, and (3) removing water from the collagen solution to produce collagen as a dry powder, wherein the collagen solution is frozen and subsequently lyophilized to remove the water.

36. The method of claim 1, wherein the collagen is undenatured.

37. The method of claim 33, wherein the collagen is undenatured.

38. The method of claim 35, wherein the collagen solution is frozen quickly in liquid nitrogen or slowly frozen at from −20° C. to −80° C.

\* \* \* \* \*